United States Patent [19]
Märkl et al.

[11] Patent Number: 5,965,431
[45] Date of Patent: Oct. 12, 1999

[54] AEROBIC BIODEGRADATION OF AROMATIC COMPOUNDS HAVING LOW WATER SOLUBILITY USING *BACILLUS THERMOLEOVORANS* STRAIN DSM 10561

[75] Inventors: Herbert Märkl, Kleckener Kirchweg 27; Garabed Antranikian, Narzissenweg 51, both of Seevetal, Germany, D-21218; Peter Becker; Samson Markossian, both of Hamburg, Germany

[73] Assignees: Herbert Märkl; Garabed Antranikian, both of Seevetal, Germany

[21] Appl. No.: 08/952,163

[22] Filed: Jan. 29, 1998

[30] Foreign Application Priority Data

Mar. 12, 1996 [DE] Germany ............... 196 09 555

[51] Int. Cl.$^6$ ............... C02F 1/00; C12N 1/00; C12N 1/20; C12N 9/00
[52] U.S. Cl. .......... 435/262.5; 210/600; 210/601; 210/632; 210/610; 435/183; 435/195; 435/198; 435/252.5; 435/262; 435/264; 435/822; 435/832
[58] Field of Search ................... 435/262, 822, 435/183, 195, 198, 252.5, 262.5, 264, 832; 210/600, 610, 601, 632

[56] References Cited

FOREIGN PATENT DOCUMENTS 0 735 005  10/1996  European Pat. Off. .

OTHER PUBLICATIONS

Sunna et al., Characterization of the xylanases from the new isolated thermophilic xylan–degrading *Bacillus thermoleovarans* strain K–3d and *Bacillus flaothermus* strain LB3A, FEMS microbiology letters, vol. 148, No. 2, abstract only, AGRICOLA data base, Mar. 15, 1997.

Feitkenhauer et al., Soil reclamation with thermophilic microorganisms, Hamb. Ber., 10 (Neue Techniken der Bodenreinigung), abstract only. CAPLUS Datatbase, 1996.
Hebenbrock et al., Biodegradation of aromatic and aliphatic hydrocarbons by thermophilic microorganisms and their cultivation in bioreactors, DECHEMA Monogr., 133 (Biodeterioration and Biodegradation), abstract only, CAPLUS database, 1996.
Novotny et al., Characterization of bacteriocins from two strains of *Bacillus thermoleovorans*, a thermophilic hydrcarbon–utilizing species. Appl. Environ. Microbiol., vol. 58, No. 8, abstract only. LIFESCI database, 1992.
Zarilla et al., *Bacillus thermoleovorans*, sp. nov., a species of obligately thermophilic hydrocarbon utilizing endospore–forming bacteria. Syst. Appl. Microbiol., vol. 9, No. 3, abstract only. LIFESCI Database, 1987.
Mutzel et al., Isolation and characaterization of a thermophilic bacillus strain, that degrades phenol and cresols as sole carbon source at 70 degrees C., Applied Microbiology and Biotech., vol. 46, No. 5–6, abstract only. BIOSIS database, 1996.
Sigurgisladottir, S. et al., "Lipase activity of thermophilic bacteria from icelandic hot springs", 1993.
Wang. Y., "Thermostable Alcaline Lipase from a newly isolated thermophilic bacillus, strain A30–1", 1995.

*Primary Examiner*—David M. Naff
*Assistant Examiner*—Deborah K. Ware
*Attorney, Agent, or Firm*—Pennie & Edmonds LLP

[57] ABSTRACT

A process for the aerobic biological break-down of substances having low water solubility in an aqueous medium, and a microorganism, Bacillus thermoleovorans strain DSM 10561 and an enzyme obtained therefrom are disclosed. The microorganism is suitable for use in the disclosed process wherein the bioavailability of the substances to be broken down is raised by setting the temperature of the aqueous medium to 45 degrees Celisus and higher. The microorganism is used to break-down the substances having low water solubility.

7 Claims, 3 Drawing Sheets

AEROBIC BIODEGRADATION OF AROMATIC COMPOUNDS HAVING LOW WATER SOLUBILITY USING *BACILLUS THERMOLEOVORANS* STRAIN DSM 10561

BACKGROUND OF THE INVENTION

The invention concerns a process for the aerobic biological break-down of substances having low water-solubility in an aqueous medium, and a new microorganism.

Processes for the aerobic break-down are generally known. For example, in wastewater purification, biological break-down of various substances occurs under aerobic conditions, whereby most of the soluble substances are adequately converted. In the case of substances having low water-solubility, however, there is the problem that in order to be broken down biologically, these must first be transferred into the aqueous phase before they can be absorbed and converted by organisms such as bacteria.

Solvents that enable break-down can be employed in order to improve the solubility of the substances to be broken down. These solvents are frequently organic compounds, which may under certain circumstances represent a significant source of environmental pollution. Thus the solvents must also be able to be broken down without leaving toxic residues and increasing the overall pollution effect.

SUMMARY OF THE INVENTION

The objective of this invention, therefore, is to avoid the use of solvents and to create an environmentally compatible, but simultaneously efficient biological process to enable the break-down of substances having low water-solubility.

According to the invention, the stated objective is achieved through increasing the bioavailability of the substances to be broken down by setting the temperature of the aqueous medium to values of 45° C. and higher, and by using a culture of thermophilic microorganisms that grow aerobically in order to brake down the substances having low water-solubility.

DETAILED DESCRIPTION OF THE INVENTION

Figure 1:
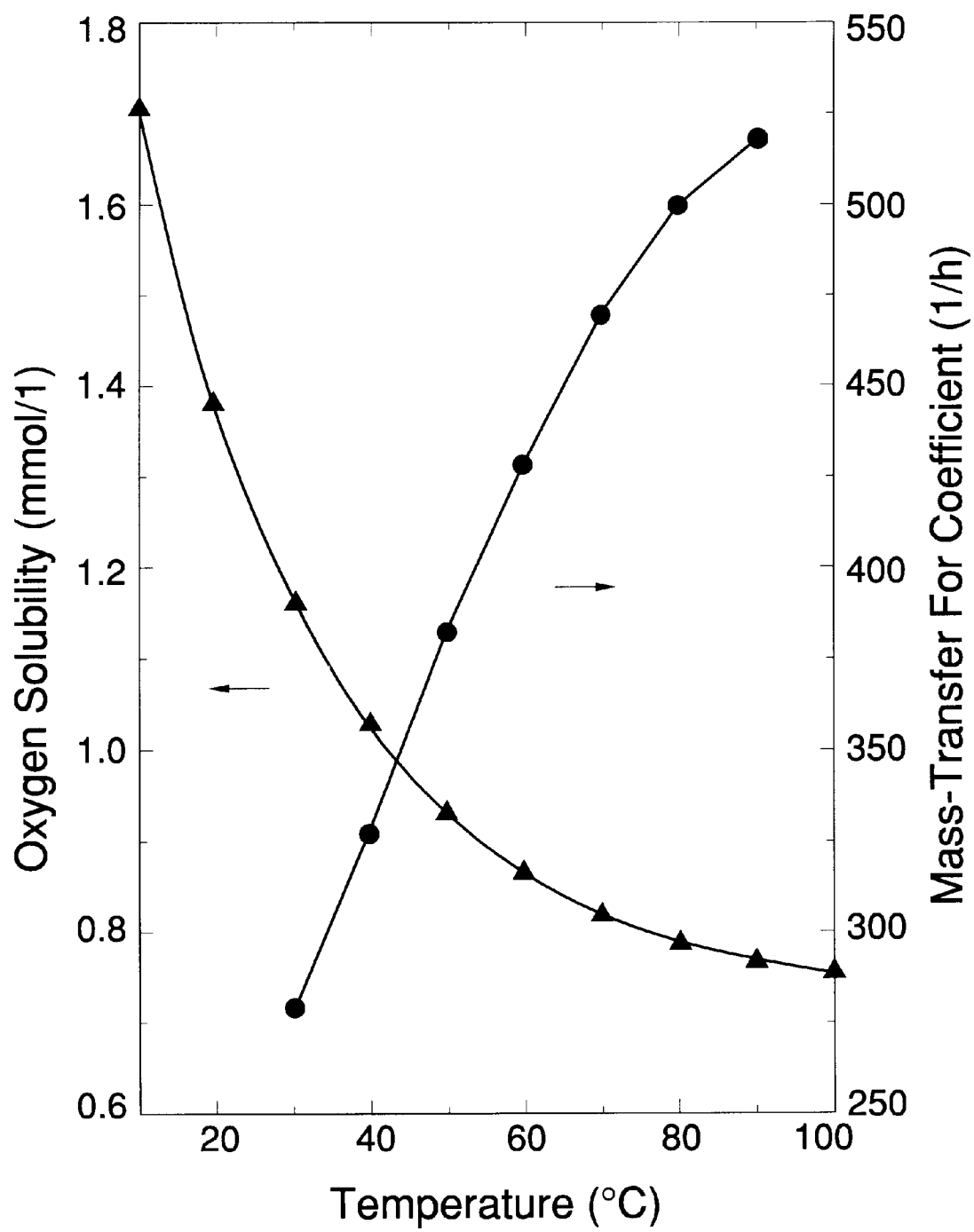
FIG. 1 is a graph showing the relationship of the oxygen solubility to the oxygen transfer coefficient with a change in temperature.

This invention is based upon the surprising discovery that not only does the bioavailability of the substances to be broken down increase with increasing temperature, but the oxygen transfer coefficient also rises at the same time. Experts have not yet recognized this discovery. On the contrary, it is consistently assumed that no efficient biological break-down can take place under aerobic conditions at higher temperatures, because oxygen solubility is too low. As shown in FIG. 1, the reduction in oxygen solubility is compensated by the increase in the oxygen transfer coefficient. Insofar it is possible to use thermophilic microorganisms even at higher temperatures and to supply these with oxygen so that they can grow aerobically. Ventilation in this case can be accomplished in the usual manner by means of air or pure oxygen.

According to one particular embodiment of the process, the temperature is increased to values above 60° C. Thermophilic microorganisms that are particularly useful for the break-down of substances with low water-solubility grow within this temperature range. The new strain IHI-91 has an optimum temperature of around 65° C. Depending upon the optimum temperature of the culture being used, the process can also be used at higher temperatures.

The process according to the invention can also be used in particular for the break-down of fats and fatty compounds with low water-solubility. These compounds should in particular include all those substances that are enzymatically divisible using lipases. However, the process according to the invention is not restricted to these compounds, but can be used in principle for all substances with low water-solubility, whose solubility increases with rising temperatures, and that can be aerobically broken down by means of thermophilic microorganisms. Examples include such substances as aromatic hydrocarbons, and especially polycyclic aromatic hydrocarbons.

The following table shows a selection from the broad substrate spectrum for aerobic thermophilic microorganisms. These substances can be easily broken down using the process according to the invention.

| Substrate | Occurence/Use |
| --- | --- |
| Tween 80 | Emulsifier |
| Silicon oil (dimethylpolysiloxane) | Antifoaming agent |
| Olive oil, triolein | Food oil production |
| Tributyrin | Softening agent |
| Palmitic acid, stearic acid | Soap production |
| Glycerin | Many uses |
| Lanolin (wool fat) | Cosmetics production |

Figure 2:
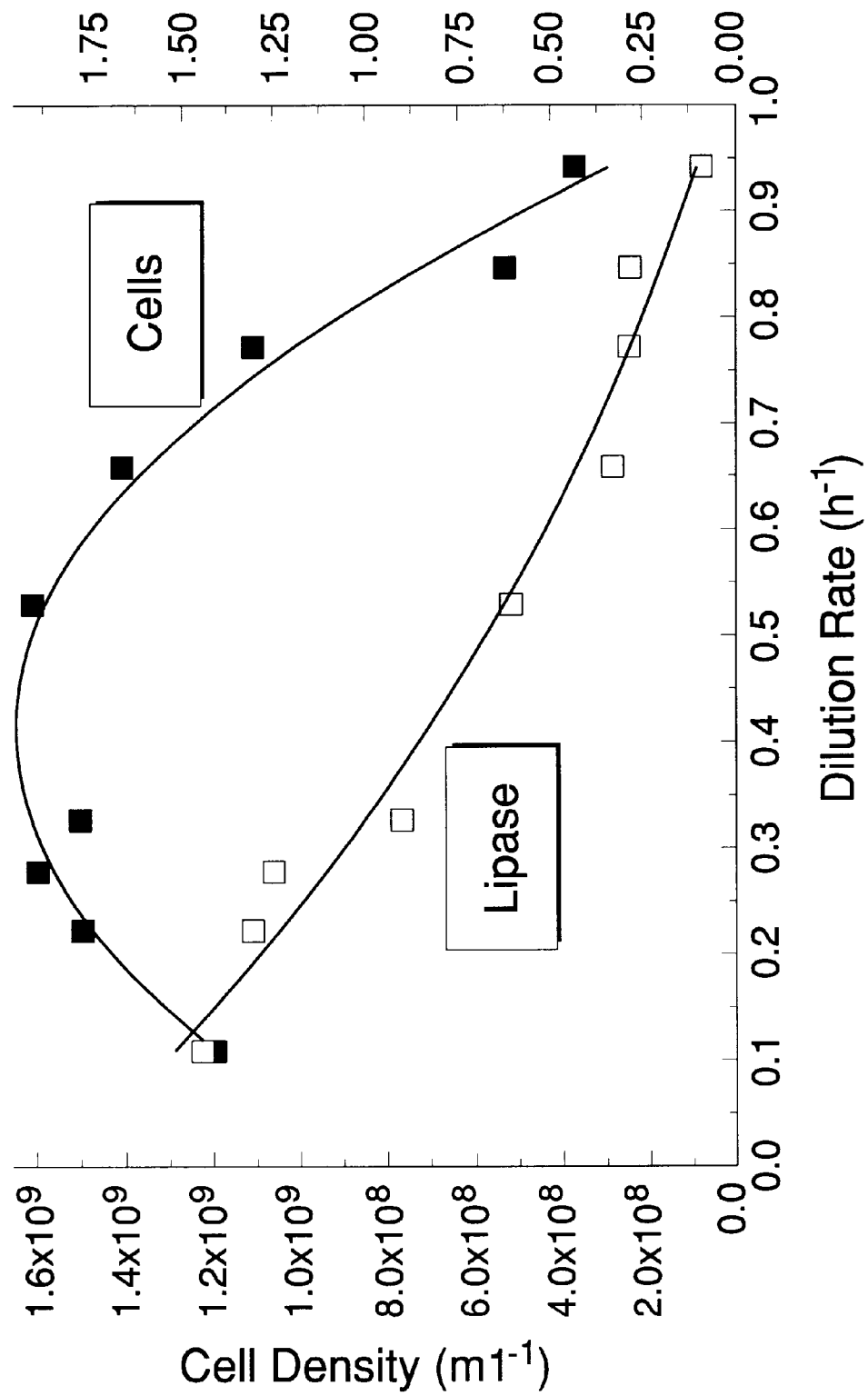
FIG. 2 is a graph showing the relationship of the cell density to the lipase activity as a function of the dilution rate.

Although the process according to the invention is not restricted to the use of a specific microorganism, the new strain IHI-91 (stored under the number DSM 10561 at DSMZ-Deutsche Sammlung von Microorganismen und Zellkulturen GmbH, D-38124, Braunschweig) was deposited on Mar. 1, 1996, at Deutsche Sammlung Von Mikroorganismen Und Zellkuturen GmbH, Mascheroder Weg 1b, D-38124 Braunschweig, Germany, under Budapest Treaty on the International Recognition of the Deposit of Microorganisms and assigned accession number DSM 10561, and has proven to be advantageous. This strain is particularly distinguishable by its lipase activity. The reaction kinetic data $K_s$ and $H_{max}$ were determined in a continuous culture of this strain, using olive oil as a substrate. The $K_s$ value for olive oil is 0.88 g/l. The maximum growth rate $H_{max}$ was calculated at 0.94 $h^{-1}$. FIG. 2 shows the result of a continuous fermentation of this strain on olive oil. The cell density and lipase activity are shown as functions of the dilution rate.

Because of the particular enzyme activity of strain IHI-91, it is also possible to obtain an enzyme composition from the culture supernatant or a suitable cell decomposition, and to use this enzyme composition to brake down substances having low water-solubility.

The process according to the invention is described in the following, using a selected experimental example.

EXAMPLE

Figure 3:
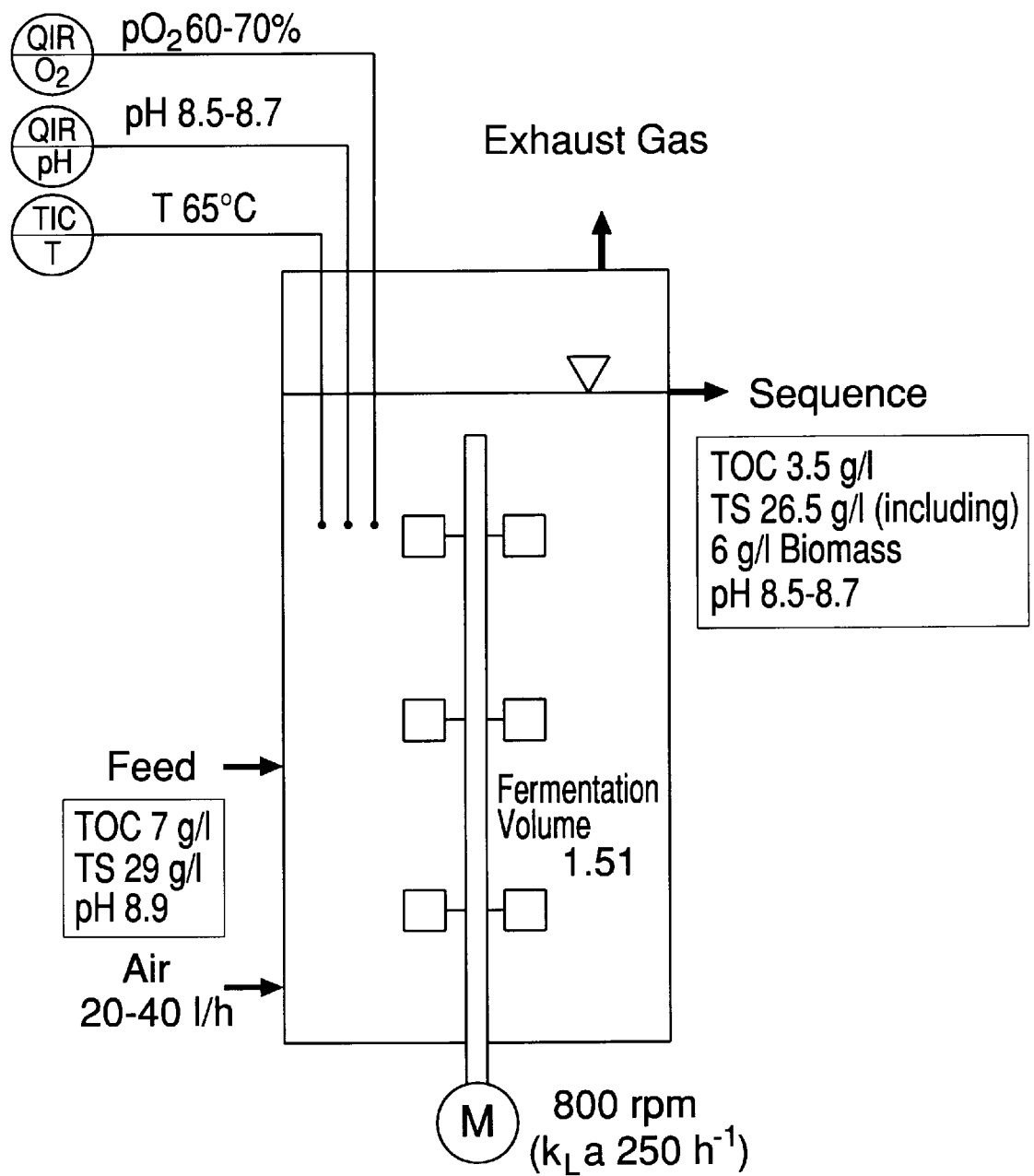
FIG. 3 is a schematic view showing the equipment setup for the method of the invention.

In this experiment, water used for washing wool in an industrial process was subjected to the process according to the invention. Wool washing water is a wastewater generated in an industrial process at temperatures ranging from 50 to 60° C., and contains a high degree of fat. This wastewater was placed into a 2-liter laboratory fermenter and heated to 65° C. It was then inoculated with the new strain IHI-91 up to a cell density of $10^9$ cells/ml. FIG. 3 shows the corresponding experiment setup. After an initial batch phase of approximately 24 hours, the procedure changed to a continuous operation with a retention time of 20 hours. During a six-day operation, solids content (TS), TOC (Total Organic Carbon) content, lipase activity, pH value, oxygen consumption, and cell density were determined. After only a short period of time, a stable biomass established itself with an organism density of approximately $10^{10}$ cells/ml, corresponding to a cell dry weight of approximately 6 g/l. During the continuous operation, a constant TOC decrease of 50% was measured, whereby oxygen consumption was established at approximately 1 g $O_2$/l and hour. At the same time, a significant reduction of the solid phase that separated on top was observed. A high level of activity by a thermophilic lipase responsible for the fat hydrolysis was detected over the entire period of the experiment.

Strain characterization (IHI-91):

The new microorganism strain IHI-91 (stored under the number DSM 10561 at DSMZ-Deutsche Sammlung von Microorganismen und Zellkulturen GmbH, D-38124, Braunschweig) can be characterized as follows:

The partial sequencing of 16SrDNA resulted in a clear classification of this strain to Group 5 of the genus Bacillus (Ash et al., Letters in Appl. Microbiol. 13, 202–206, 1991). A similarity of 99.8% was established with the species *Bacillus kaustophilus, Bacillus thermoleovorans, Bacillus caldotenax,* and *Bacillus caldolyticus.*

Based on its physiological features, the microorganism strain IHI-91 of the species *Bacillus thermoleovorans* is the most similar. This classification was confirmed with a value of 82.5% through DNA/DNA hybridization.

| Characteristics of strain IHI-91: | |
|---|---|
| Cell form | rod |
| width in µm | 0.7–0.8 |
| length in µm | 2.5–5.0 |
| Spores | |
| ellipsoid | + |
| round | − |
| swollen | v |
| Catalase | + |
| Anaerobic growth | − |
| VP reaction | n.g. |
| Optimal temperature | |
| Growth positive at ° C. | 65 |
| Growth negative at <° C. | 45 |
| Acid from | |
| D-glucose | + |
| L-arabinose | + |
| D-xylose | − |
| D-mannitol | + |
| D-fructose | + |
| Gas from glucose | − |
| Lecithinase | n.g. |
| Hydrolysis of | |
| Starch | + |
| Gelatin | + |
| Casein | + |
| Tween 80 | + |
| Esculin | − |
| Utilization of | |
| Citrate per Koser | + |
| Propionate | + |
| Break-down of tyrosine | − |
| $NO_2^-$ from $NO_3^-$ | + |
| Indole | − |
| Phenylalanine desaminase | − |
| Arginine dihydrolase | − |
| Urease | + |

Abbreviations:
n.g. no growth
v variable
Fatty acid profile:
The characteristic fatty acids for the genus Bacillus were detected.

We claim:

1. A process for the aerobic biodegradation in an aqueous medium of a compound or mixture of compounds having a predetermined bioavailability and low water solubility, comprising the steps of:

a) increasing the bioavailability of the compound or mixture of compounds to be degraded by setting the aqueous medium to temperature values of 45° C. and higher; and b) using a culture of aerobically growing thermophilic *Bacillus thermoleovorans* strain DSM 10561 to degrade said compound or mixture of compounds having low water solubility.

2. The process according to claim 1, wherein the temperature is set to values above 60° C.

3. The process according to claim 1, wherein said compounds having low water solubility are fats and fatty compounds.

4. The process according to claim 1, wherein said compounds having low water solubility are aromatic hydrocarbons and/or polycyclic aromatic hydrocarbons.

5. A biologically pure culture of a microorganism *Bacillus thermoleovorans* strain IHI-91 having accession number DSM 10561.

6. An enzyme composition obtained from the microorganism according to claim 5 and suitable for the biodegradation of a compound or mixture of compounds having low water solubility, wherein said compound or mixture of compounds comprises aromatic hydrocarbons and/or polycyclic aromatic compounds.

7. An enzyme composition obtained from a microorganism *Bacillus thermoleovorans* of strain IHI-91 and having accession number DSM 10561 wherein the enzyme composition demonstrates lipase activity and is suitable for the biodegradation of a compound or mixture of compounds having low water solubility, wherein said compound or mixture of compounds comprises aromatic hydrocarbons and/or polycyclic aromatic compounds.

* * * * *

UNITED STATES PATENT AND TRADEMARK OFFICE
CERTIFICATE OF CORRECTION

PATENT NO. : 5,965,431

DATED : October 12, 1999

INVENTOR(S) : Herbert Märkl et al.

It is certified that error appears in the above-identified patent and that said Letters Patent is hereby corrected as shown below:

TITLE PAGE, after "196 09 555" in the Foreign Application Priority Data, insert the following line

```
Item [22] PCT Filed:            March 11, 1997
     [86] PCT No:               PCT/DE97/00461
          371 Date:             Jan. 29, 1998
          102(e) Date:          Jan. 29, 1998

[87] PCT Pub. No:          WO/97-33838
          PCT Pub. Date:        Sept. 18, 1997
```

Signed and Sealed this

Twenty-third Day of May, 2000

Attest:

Q. TODD DICKINSON

*Attesting Officer*  *Director of Patents and Trademarks*